United States Patent [19]
Tomilov

[11] 3,972,227
[45] Aug. 3, 1976

[54] METHOD OF ULTRASONIC MEASUREMENTS

[76] Inventor: Boris Vasilievich Tomilov, ulitsa Chkalova, 9, kv. 74, Khabarovsk, U.S.S.R.

[22] Filed: Apr. 5, 1974

[21] Appl. No.: 458,400

[52] U.S. Cl. .................................. 73/67.7; 73/1 DV
[51] Int. Cl.² .......................................... G01N 29/00
[58] Field of Search ............... 73/67.7, 67.6, 67.5 R, 73/67.8 R, 67.8 S, 67.9, 71.5 US, 1 DV; 310/8.1, 8.7, 9.1; 116/137 A

[56] References Cited
UNITED STATES PATENTS

| | | | |
|---|---|---|---|
| 2,667,780 | 2/1954 | Van Valkenburg | 73/67.9 |
| 3,741,003 | 6/1973 | Gunkel | 73/67.7 |
| 3,759,090 | 9/1973 | McFaul et al. | 73/67.9 |
| 3,791,199 | 2/1974 | Toth et al. | 73/67.9 |
| 3,813,926 | 6/1974 | Stubbeman | 73/67.7 |

Primary Examiner—Richard C. Queisser
Assistant Examiner—Stephen A. Kreitman
Attorney, Agent, or Firm—Haseltine, Lake & Waters

[57] ABSTRACT

A method for non-destructive testing and for quality checking solid materials in which an acoustic contact is formed during the measurement between a converter and the material, this contact being stabilized by imparting vibratory oscillations to the converter relative to the material being tested. Then the moment of the formation of a high-quality acoustic contact is determined by an abrupt decrease in the rate of the test signal amplitude change. The vibration is discontinued, and depending upon the accuracy of measurement required, the test signal parameters, which carry information on the properties of the article being tested are measured either directly upon interrupting the vibration, or after a time interval sufficient to reduce the internal stress of the converter created due to its deformation resulting from vibration and pressure against the article.

2 Claims, 1 Drawing Figure

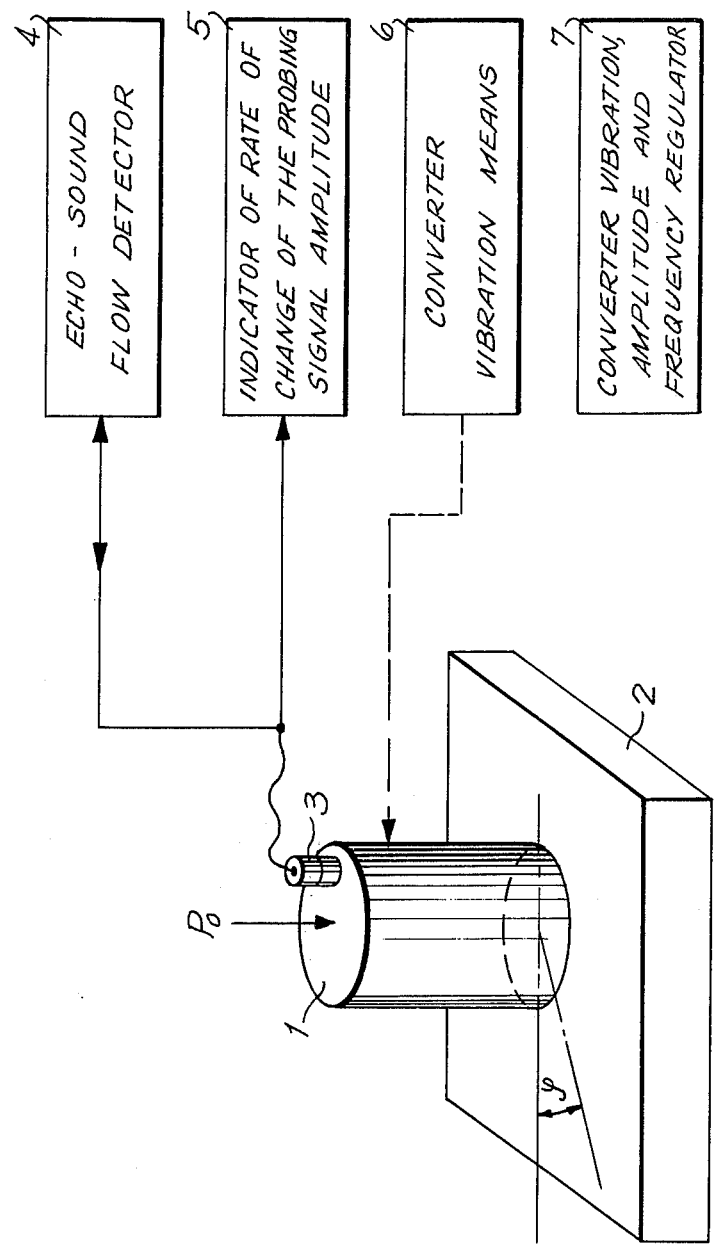

METHOD OF ULTRASONIC MEASUREMENTS

The present invention relates to measuring techniques, and more particularly to a method of ultrasonic measurement for the purpose of non-destructive testing of materials and articles.

Known in the art are methods of ultrasonic measurements used in measuring thickness, in flaw detection and the like, e.g. contact, immersion and contact-immersion methods.

The contact method of ultrasonic measure consists in that the surface of an article is preliminarily coated with a layer of liquid or semi-liquid lubricant (water, oil, solid oil, glycerine and the like). Then an acoustic converter is placed in intimate contact with the article through this layer, ultrasonic signals are introduced into the article, and the reflected signals are received which carry information regarding the properties of the article being tested.

The immersion method of ultrasonic measurements consists in that a thick layer of liquid (water, oil) is placed between the converter and the surface of the article being tested, the introduction of the ultrasonic signals into the article and their reception being effected through said liquid layer.

The contact-immersion method of ultrasonic measurements involves the use of a multilayer interface medium formed by an elastic film and a liquid or semi-liquid lubricant, the contact with the article surface being effected through the film which is in some cases coated with an oily lubricant.

Where the contact and contact-immersion methods of ultrasonic measurements are used, the parameters of the resulting acoustic contacts substantially depend upon the degree of pressure of the converter against the article being tested, the purity and uniformity of the lubricant, the orientation of the converter with respect to the surface of the article being tested, that is, they are determined by individual actions of the operator and by test conditions. The main disadvantage of this method lies in the dependence of the parameters of the acoustic contact upon a large number of external factors including the physical state of the operator. In addition, the contact quality is not controlled in these cases.

This results in considerable errors in the rate measurement, and in particular in measuring the rate of ultrasonic damping, as well as in the appearance of uncontrollable distortions of the test signal spectrum and, finally in insufficient reliability of the quality check of the articles.

The immersion method ensures a stable and reproducible acoustic contact, but it requires the use of immersion baths, and a large consumption of immersion liquids, this method not allowing for detailed study of articles of intricate shape because of difficulties encountered in making the scanning device of the converter.

Where the contact method of ultrasonic measurements is used, the operator would normally perform several movements at the instant of pressing the converter against the article being tested to lap the converter surface with the article surface, whereby the quality of the resulting acoustic contact is somewhat improved.

However, this method of forming the acoustic contact cannot provide for the contact quality necessary to obtain reliable results, the parameters of the contact being casual for each test, and considerable errors are present in the measurement results.

It is an object of the invention to provide a method of ultrasonic measurements for the purpose of non-destructive testing of solid materials, wherein the error of measurement is reduced.

It is another object of the invention to provide a method of ultrasonic measurements, wherein the quality of the acoustic contact between the converter and the article being tested is improved.

Still another object of the invention is to provide a method of ultrasonic measurements, wherein constant parameters of the acoustic contact between the converter and the article being tested are insured from one test to another.

Furthermore, it is an object of the invention to provide a method of ultrasonic measurements, wherein reliable check the quality on non-metallic materials, such as building materials is ensured without using a lubricant.

The above objects are accomplished in that in a method of ultrasonic measurements for the purpose of non-destructive testing of solid materials, comprising the step of placing an electromechanical converter in intimate acoustic contact with the article being tested under a constant pressure, while imparting mutual vibratory oscillations thereto, and passing an ultrasonic test signal through the material being tested, according to the invention the rate of change of the test signal amplitude is observed during the test, and the vibration is discontinued upon an abrupt decrease in the rate of change of the amplitude, and the test signal parameters are measured which carry information regarding the properties of the article being tested.

The invention ensures obtaining maximum possible intimate contact between the converter and the article, a minimum thickness of the contact layer and uniform distribution of lubricant in the contact layer.

The invention allows reliable evaluation of the quality of the acoustic contacts obtained during the tests.

This permits improving the accuracy of the ultrasonic measurements and to increase the reliability of the assessment of quality of the articles and materials being tested.

Another embodiment of the invention consists in that the test signal parameters are measured after a time interval sufficient to remove the internal stress of the converter created due to its vibration and to the pressure thereupon.

Measurement of the test signal parameters which carry information regarding the properties of the materials being tested after the time interval for removing the internal stress of the converter makes it possible to obtain the measurement information at stabilized values of the parameters of the acoustic contacts, the measurement results incorporating minimum errors.

Other objects and advantages of the invention will be apparent from the following detailed description given with reference to the appended drawing, the sole FIGURE of which is a diagrammatic illustration of the method of the invention.

The surface of an article 2 which is to be tested is coated with a thin layer of lubricant. An electromechanical converter is applied with constant pressure against the article and a device for vibrating the converter relative to the article is mounted on the article surface and fixed thereto. Upon energizing of a test signal generator 4, introduction of the signal into the article is effected via connecter 3–4, and reception of the signal reflected by the article 4 is received by the detector, the amplitude of the signal is observed using a receiver display indicator 5, such as an electron-beam indicator or a voltmeter.

Then a vibratory motion relative to the article is imparted to the converter by device 6 in the segment 4–7, and the rate of growth of the amplitude of the received signal is observed at indicator 5. During the vibration of the rate of the amplitude growth is steadily decreasing.

Finally, there comes a moment, when the rate of the test signal amplitude growth abruptly decreases. This indicates the formation of the intimate and thin contact layer between the converter and the article, that is, the formation of a high-quality acoustic contact therebetween, thus determining the instant at which the converter vibration should be discontinued.

Upon the interruption of the vibration, the test signal parameters can be measured with the accuracy sufficient for the majority of practical applications.

For obtaining a better accuracy of measurement, it is necessary to wait during a certain time interval after the interruption of the vibration, during which the internal stress of the converter 1 is substantially reduced, said stress resulting from converter deformation due to its pressure against the article and to vibration.

In practice, the measurement of the test signal parameters which carry information on the properties of the article being tested should be performed when the rate of variation of the test signal amplitude has become near or equal to zero, which indicates the completion of transient processes in the acoustic contact and the establishment of steady conditions.

In this case improved accuracy of measurement is obtained as compared to the case, where the signal parameters are measured directly upon interrupting the vibration.

The use of the method according to the invention in measuring thickness permits avoiding considerable errors in determining the article thickness due to non-uniform thickness of the contact layer.

Where the contact measurement of ultrasonic damping is to be performed for non-uniform materials with a rough finish of the articles, the method according to the invention cannot be substituted by any other method.

What is claimed is:

1. A method of ultrasonic measurements for the purpose of non-distructive testing of solid materials and articles, comprising the steps of placing an electromechanical converter in intimate acoustic contact with the article being tested under a constant pressure, imparting mutual vibratory oscillations to said electromechanical converter while; passing an ultrasonic test signal to said article through said converter; observing the rate of change of the amplitude of said test signal and discontinuing said mutual vibratory oscillations to said converter upon an abrupt decrease in the rate of change of said ultrasonic test signal amplitude, and subsequently measuring the parameters of said test signal which carry information on the properties of the article being tested.

2. A method as claimed in claim 1, wherein the test signal parameters are measured after interrupting the vibration of the converter over a time interval sufficient to remove the internal stress of the converter created due to vibration and pressure.

* * * * *